US007816384B2

(12) United States Patent
Werner et al.

(10) Patent No.: US 7,816,384 B2
(45) Date of Patent: *Oct. 19, 2010

(54) METHOD FOR TREATING A DEMYELINATING CONDITION

(75) Inventors: Peter Werner, New York, NY (US); David Pitt, Bronx, NY (US); Elimor Brand-Schieber, White Plains, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/290,423

(22) Filed: Oct. 30, 2008

(65) Prior Publication Data

US 2009/0069290 A1 Mar. 12, 2009

Related U.S. Application Data

(63) Continuation of application No. 10/223,068, filed on Aug. 16, 2002, now Pat. No. 7,470,718, which is a continuation-in-part of application No. 09/678,686, filed on Oct. 3, 2000, now Pat. No. 6,455,553.

(51) Int. Cl.
*A61K 31/44* (2006.01)
(52) U.S. Cl. ...................... 514/356; 514/428
(58) Field of Classification Search ................. 514/356, 514/428
See application file for complete search history.

(56) References Cited

U.S. PATENT DOCUMENTS

| | | | |
|---|---|---|---|
| 5,990,103 | A | 11/1999 | Schonharting et al. |
| 6,187,756 | B1 | 2/2001 | Lee et al. |
| 6,190,691 | B1 | 2/2001 | Mak |
| 6,277,850 | B1 | 8/2001 | Lubisch et al. |
| 6,337,325 | B1 | 1/2002 | Schonharting et al. |
| 6,455,553 | B1 * | 9/2002 | Werner et al. ............... 514/356 |
| 6,531,464 | B1 | 3/2003 | Szabo et al. |
| 7,470,718 | B2 * | 12/2008 | Werner et al. ............... 514/428 |

FOREIGN PATENT DOCUMENTS

| | | |
|---|---|---|
| WO | WO 92/07564 A2 | 5/1992 |
| WO | WO 00/01376 A2 | 1/2000 |
| WO | WO 01/87280 A2 | 11/2001 |

OTHER PUBLICATIONS

Gilmore et al. Journal of Neurology, Neurosurgery, and Psychiatry, 1985, vol. 48, pp. 1140-1146.*
Komoly et al. J. Neurol., 1986, vol. 233, pp. 59-60.*
Jensen. Journal of the Oslo City Hospitals, Jun.-Jul. 1989, vol. 39, pp. 67-73 (Abstract attached).*
Sa. Journal of Neuroimmunology, 1995, vols. 56-63, Supplement 1, p. 61.*
Medline An 95354533, Ditzen et al, Deutsche Medizinische Wochenschrift, Jul. 28, 1995, 120 (30) 1061-2, abstract.
Akassoglou, K., et al, Oligodendrocyte Apoptosis and Primary Demyelination Induced by Local TNF/p55TNF Receptor Signaling in the Central Nervous System of Transgenic Mice, American Journal of Pathology, 153:801-813 (1998).
Canella, B., et al, The neuregulin, glial growth factor 2, diminishes autoimmune demyelination and enhances remyelination in a chronic relapsing model for multiple sclerosis, Proc. Natl. Acad. Sci. USA, 95:10100-10105 (1998).
Mason, R.P., et al, Inhibition of Excessive Neuronal Apoptosis by the Calcium Antagonist Amlodipine and Antioxidants in Cerebellar Granule Cells, Journal of Neurochemistry, 72:1448-1456 (1999).
McDonald, J. W., et al, Oligodendrocytes from forebrain are highly vulnerable to AMPA/kainate receptor-mediated excitotoxicity, Nat. Med., 4:291-297 (1998).
Piani, D., et al, Murine brain macrophages induced NMDA receptor mediated neurotoxicity in vitro by secreting glutamate, Neurosci. Lett., 133:159-162 (1991).
Pitt, D., et al, Glutamate excitotoxicity in a model of multiple sclerosis, Nat. Med., 6:67-70 (2000).
Rayner, D.C., et al, Major histocompatability complex class II-restricted cytotoxicity by self-myelin basic protein-reactive T-cell hybridomas: evidence for a tumour necrosis factor-independent nucleolytic mechanism, Immunology, 78:273-278 (1993).

(Continued)

*Primary Examiner*—James D Anderson
(74) *Attorney, Agent, or Firm*—Amster, Rothstein & Ebenstein LLP (57) ABSTRACT

Methods for treating a demyelinating condition in a subject in need of treatment are provided. In some aspects the methods encompass administering to the subject an amount of a $Ca^{2+}$-channel blocker effective to treat the demyelinating condition. In other aspects, the methods encompass administering to the subject an amount of a glutamate inhibitor effective to treat the demyelinating condition. In additional aspects, the methods encompass administering to the subject a $Ca^{2+}$-channel blocker in combination with a glutamate inhibitor, in amounts effective to treat the demyelinating condition. In still other aspects, the methods encompass administering to the subject a $Ca^{2+}$-channel blocker in combination with a hypertensive agent, in amounts effective to treat the demyelinating condition. Also provided are pharmaceutical compositions having a $Ca^{2+}$-channel blocker, a glutamate inhibitor, and a pharmaceutically-acceptable carrier. Additionally, pharmaceutical compositions having a $Ca^{2+}$-channel blocker, a hypertensive agent, and a pharmaceutically-acceptable carrier are provided.

9 Claims, 5 Drawing Sheets

OTHER PUBLICATIONS

Waxman, S.G., et al, Protection of the axonal cytoskeleton in anoxic optic nerve by decreased extracellular calcium, Brain Res., 614:137-145 (1993).

Werner, P., et al, Glutamate excitotoxicity—a mechanism for axonal damage and oligodendrocyte death in Multiple Sclerosis?, J. Neural Transm. Suppl., 60:375-385 (2000).

Brand-Schieber, E. et al., Ca2+ Blockers Ameliorate Disease in Mouse Model of Multiple Sclerosis (MS), J. Neurochemistry, 81:50 (Jun. 22, 2002).

Brosnan and Raine, Mechanisms of Immune Injury in Multiple Sclerosis. Brain Pathology. vol. 6. pp. 243-257 (1996).

El-Fawal H.A.N. et al., Effect of Verapamil on Organophosphorus—Induced Delayed Neuropathy in Hens. Toxicology and Applied Pharmacology. vol. 97. pp. 500-511 (1989).

Flanagan E.M. et al., Neurotoxin Quinolinic Acid Is Selectively Elevated in Spinal Cords of Rats with Experimental Allergic Encephalomyelitis. Journal of Neurochemistry. vol. 64. No. 3. pp. 1192-1196 (1995).

WPIDS AN 1998-053370, Behl et al, DE19624808 A1, Jan. 2, 1998, abstract.

* cited by examiner

FIG. 1

METHOD FOR TREATING A DEMYELINATING CONDITION

CROSS-REFERENCE TO RELATED APPLICATION

This application is a Continuation of U.S. patent application Ser. No. 10/223,068, filed Aug. 16, 2002, now U.S. Pat. No. 7,470,718, which is a Continuation-in-Part of U.S. patent application Ser. No. 09/678,686, filed Oct. 3, 2000, now U.S. Pat. No. 6,455,553.

STATEMENT REGARDING FEDERALLY SPONSORED RESEARCH

The invention was supported by NIH Grant Application Nos. NS41056 and NS07098. As such, the U.S. Government has certain rights in the invention.

BACKGROUND OF THE INVENTION (1) Field of the Invention

The present invention generally relates to treatments of demyelinating conditions. More specifically, the invention relates to the use of calcium channel blockers for treating demyelinating conditions, especially multiple sclerosis.

(2) Description of the Related Art

REFERENCES CITED

Akassoglou et al. Oligodendrocyte apoptosis and primary demyelination induced by local TNF/p55TNF receptor signaling in the central nervous system of transgenic mice: models for multiple sclerosis with primary oligodendrogliopathy. Am. J. Path. 153(3):801-13, 1998.

Bar-Or et al. Molecular pathogenesis of multiple sclerosis. J. Neuroimmunol. 100:252-59, 1999.

Beers and Berkow, eds. The Merck Manual of Diagnosis and Therapy, 17$^{th}$ ed. 1299, 1437, 1473-76, 1483. Merck Research Laboratories, Whitehouse Station, N.J., 1999.

Brand-Schieber, E. and P. Werner. $Ca^{2+}$ blockers ameliorate disease in mouse model of multiple sclerosis (MS). J. Neurochem. 81:50 (2002).

Brown, A.M., R. E. Westenbroek, W. A. Catterall, and B. R. Ransom. Axonal L-type $Ca^{2+}$ channels and anoxic injury in rat CNS white matter. J. Neurophysiol. 85:900-911, 2001.

Cannella et al. The neuregulin, glial growth factor 2, diminishes autoimmune demyelination and enhances remyelination in a chronic relapsing model for multiple sclerosis. Proc. Natl. Acad. Sci. USA 95:10100-105, 1998.

Choi, D. W. Calcium-mediated neurotoxicity: relationship to specific channel types and role in ischemic damage. Trends Neurosci. 11:465-69, 1988.

Agrawal, S. K., R. Nashmi, and M. G. Fehlings. Role of L- and N-type calcium channels in the pathophysiology of traumatic spinal cord white matter injury. Neurosci. 99:179-188, 2000.

Claudio, L., Y. Kress, J. Factor, and C. F. Brosnan. Mechanisms of edema formation in experimental autoimmune encephalomyelitis. The contribution of inflammatory cells. Am. J. Pathol. 137:1033-1045, 1990.

DiBiase et al. Adrenoleukodystrophy: genetics, phenotypes, pathogenesis, and treatment. Ann. Ist. Super Sanita 35:185-92, 1999.

Ewing, C. and C. C. A. Bernard. Insights into the aetiology and pathogenesis of multiple sclerosis. Immunol. Cell. Biol. 76:47-54, 1998.

Fujimoto, T., S. Sakoda, H. Fujimura, and T. Yanagihara. Ibudilast, a phosphodiesterase inhibitor, ameliorates experimental autoimmune encephalomyelitis in Dark August rats. J. Neuroimmunol. 95:35-42, 1999.

Genain et al. Identification of autoantibodies associated with myelin damage in multiple sclerosis. Nature Medicine 5(2):170-75, 1999.

Gill, A., S. F. Flaim, B. P. Damiano, S. P. Sit, and M. D. Brannan. Pharmacology of bepridil. Am. J. Cardiol. 69:11D-16D, 1992.

Glabinski, A. R., M. Tani, V. K. Tuohy and R. M. Ransohoff. Murine experimental autoimmune encephalomyelitis: a model of immune-mediated inflammation and multiple sclerosis. Methods Enzymol. 288:182-190, 1997.

Gold et al., Animal models for autoimmune demyelinating disorders of the nervous system. Mol. Med. Today 6:88-91, 2000.

Hardin-Pouzet et al., Glutamate metabolism is down-regulated in astrocytes during experimental autoimmune encephalomyelitis. Glia 20:79-85, 1997.

Hartung, H.-P., Pathogenesis of inflammatory demyelination: implications for therapy. Current Opinion in Neurology 8:191-99, 1995.

Imaizumi, T., J. D. Kocsis, and S. G. Waxman. 1999. The role of voltage-gated $Ca^{2+}$ channels in anoxic injury of spinal cord white matter. Brain Res. 817:84-92.

Juhler, M. Pathophysiological aspects of acute experimental allergic encephalomyelitis. Acta Neurol Scand. 78:1-21, 1988.

Jung, S., J. Zielasek, G. Kollner, T. Donhauser, K. Toyka, and H. P. Hartung. Preventive but not therapeutic application of Rolipram ameliorates experimental autoimmune encephalomyelitis in Lewis rats. J. Neuroimmunol. 68:1-11, 1996.

Kolb and Kolb-Bachofen. Nitric oxide: a pathogenic factor in autoimmunity. Immunol. Today, 13(5): 157-60, 1992.

Kornek, B., M. K. Storch, R. Weissert, E. Wallstroem, S. Andreas, T. Olsson, C. Linington, M. Schmidbauer, and H. Lassmann. Multiple sclerosis and chronic autoimmune encephalomyelitis. A comparative quantitative study of axonal injury in active, inactive and remyelinated lesions. Am. J. Pathol. 157:267-276, 2000.

Kornek, B., M. K. Storch, J. Bauer, A. Djamshidian, R. Weissert, E. Wallstroem, A. Stefferl, F. Zimprichi, C. Linington, M. Schmidbauer, and H. Lassmann. Distribution of a calcium channel subunit in dystrophic axons in multiple sclerosis and experimental autoimmune encephalomyelitis. Brain. 124:1114-1124, 2001.

Krivit et al. Bone marrow transplantation for globoid cell leukodystrophy, adrenoleukodystrophy, metachromatic leukodystrophy, and Hurler syndrome. Curr. Opin. Hematol., 6:377-82, 1999.

Lassmann, H. Mechanisms of demyelination and tissue damage in multiple sclerosis. Acta. Neurol. Belg. 99:6-10, 1999.

Levine, S., J. Simon, and E. J. Wenk. Edema of the spinal cord in experimental allergic encephalomyelitis. Proc. Soc. Exp. Biol. Med. 123:539-541, 1966.

Li, S., Q. Jiang, and P. K. Stys. Important role of reverse $Na^+$-$Ca^{2+}$ exchange in spinal cord white matter injury at physiological temperature. J. Neurophysiol. 84:1116-1119, 2000.

Liedtke et al. Effective treatment of models of multiple sclerosis by matrix metalloproteinase inhibitors. Ann. Neurol. 44:35-46, 1998.

Liu, H.-N., E. Molina-Holgado, and G. Almazan. Glutamate-stimulated production of inositol phosphates is mediated by Ca²⁺ influx in oligodendrocyte progenitors. Eur. J. Pharmacol. 338:227-287, 1997.

Mason et al. Inhibition of excessive neuronal apoptosis by the calcium antagonist amlodipine and antioxidants in cerebellar granule. J. Neurochem., 72(4):1448-56, 1999.

Matute, C., M. Domercq, D. J. Fogarty, M. P. de Zulueta, and M. V. Sanchez-Gomez. On how altered glutamate homeostasis may contribute to demyelinating disease in the CNS. The functional role of glial cells in health and disease. Matsas and Tsacopoulos, Eds. Kluer Academic/Plenum Publishers, New York. 97-107, 1999.

McDonald et al. Oligodendrocytes from forebrain are highly vulnerable to AMPA/Kainate receptor-mediated excitotoxicity. Nature Medicine 4(3):291-97, 1998.

The Merck Index. Merck and Co., Inc., Rahway, N.J., 1989.

Mokhtarian, F., D. E. McFarlin, and C. S. Raine. Adoptive transfer of myelin basic protein-sensitized T cells produces chronic relapsing demyelinating disease in mice. Nature 309:356-358, 1984.

Morrissey, S. P., H. Stodal, U. Zettle, C. Simonis, S. Jung, R. Kiefer, H. Lassmann, H.-P. Hartung, A. Haase and K. V. Toyka. In vivo MRI and its histological correlates in acute adoptive transfer experimental allergic encephalomyelitis. Quantification of inflammation and edema. Brain 119:239-248, 1996.

Niino, M., K. Iwabuchi, S. Kikuchi, M. Ato, T. Morohashi, A. Ogata, K. Tashiro, and K. Onoé. Amelioration of experimental autoimmune encephalomyelitis in C57B1/6 mice by an agonist of peroxisome proliferator-activated receptor-γ. J. Neuroimmunol. 116:40-48, 2001.

Njenga and Rodriguez. Animal models of demyelination. Current Opinion in Neurology 9:159-64, 1996.

Physicians' Desk Reference, 54ᵗʰ ed. Medical Economics Company, Inc., Montvale, N.J. 2000.

Piani et al. Murine brain macrophages induce NMDA receptor mediated neurotoxicity in vitro by secreting glutamate. Neurosci. Lett., 133:159-62, 1991.

Pithon et al. Glutamine utilization by rat neutrophils: presence of phosphate-dependent glutaminase. Am. J. Phys., 273: C1124-29, 1997.

Pitt et al., Glutamate excitotoxicity in a model of multiple sclerosis. Nature Medicine 6(1):67-70, 2000.

Prineas and McDonald, Demyelinating Diseases. In Greenfield's Neuropathology, 6ᵗʰ ed. 813-81. Edward Arnold: New York, 1997.

Raine, C. S., The lesion in multiple sclerosis and chronic relapsing experimental allergic encephalomyelitis: a structural comparison. In Multiple Sclerosis Clinical and Pathogenetic Basis, Raine, C. S., McFarland, H. F., and Tourtellotte, W. W., eds. 243-86. Chapman & Hall, London, 1997.

Raine, C. S., F. Mokhtarian and D. E. McFarlin. Adoptively transferred chronic relapsing experimental autoimmune encephalomyelitis in the mouse. Lab. Invest. 51:534-546, 1984.

Rosenberg, L. J., Y. D. Teng, and J. R. Wrathall. Effects of the sodium channel blocker tetrodotoxin on acute white matter pathology after experimental contusive spinal cord injury. J. Neurosci. 19:6122-6133, 1999.

Rothman and Olney. Excitotoxicity and the NMDA receptor. TINS 10:299-302, 1987.

Simmons, R. D., C. C. A. Bernard, G. Singer, and P. R. Carnegie. Experimental autoimmune encephalomyelitis. An anatomically-based explanation of clinical progression in rodents. J. Neuroimmunol. 3:307-318, 1982.

Stys, P. K. Anoxic and ischemic injury of myelinated axons in CNS white matter: from mechanistic concepts to therapeutics. J. Cereb. Blood Flow Metab. 18:2-25, 1998.

Stys, P. K. and R. M. Lopachin. Mechanisms of calcium and sodium fluxes in anoxic myelinated central nervous system axons. Neurosci. 82:21-32, 1998.

Trapp et al. Axonal transection in the lesions of multiple sclerosis. N. Engl. J. Med., 338:278-85, 1998.

Wakefield, A. J., L. J. More, J. Difford and J. E. McLaughlin. Immunohistochemical study of vascular injury in acute multiple sclerosis. J. Clin. Pathol. 47:129-133, 1994.

Waxman, S. G., J. A. Black, B. R. Ransom, and P. K. Stys. Protection of the axonal cytoskeleton in anoxic optic nerve by decreased extracellular calcium. Brain Res. 614:137-145, 1993.

Wender, R., A.M. Brown, R. Fern, R. A. Swanson, K. Farrell, and B. R, Ransom. Astrocytic glycogen influences axon function and survival during glucose deprivation in central white matter. J. Neurosci. 20:6804-6810, 2000.

PCT patent publication WO 92/07564.

Demyelination is a feature of many neurologic disorders. Demyelinating conditions are manifested in loss of myelin—the multiple dense layers of lipids and protein which cover many nerve fibers. These layers are provided by oligodendroglia in the central nervous system (CNS), and Schwann cells in the peripheral nervous system. In patients with demyelinating conditions, demyelination may be irreversible; it is usually accompanied or followed by axonal degeneration, and often by cellular degeneration. Demyelination can occur as a result of neuronal damage or damage to the myelin itself—whether due to aberrant immune responses, local injury, ischemia, metabolic disorders, toxic agents, or viral infections (Prineas and McDonald, 1997; Beers and Berkow, 1999).

Central demyelination (demyelination of the CNS) occurs in several conditions, often of uncertain etiology, that have come to be known as the primary demyelinating diseases. Of these, multiple sclerosis is the most prevalent. Other primary demyelinating diseases include adrenoleukodystrophy, adrenomyeloneuropathy, AIDS-vacuolar myelopathy, HTLV-associated myelopathy, Leber's hereditary optic atrophy, progressive multifocal leukoencephalopathy, subacute sclerosing panencephalitis, and tropical spastic paraparesis. In addition, there are acute conditions in which demyelination can occur in the CNS, e.g., acute disseminated encephalomyelitis and acute viral encephalitis. Furthermore, acute transverse myelitis, a syndrome in which an acute spinal cord transection of unknown cause affects both gray and white matter in one or more adjacent thoracic segments, can also result in demyelination. Finally, there are animal models which mimic features of human demyelinating diseases (Beers and Berkow, 1999). Examples include experimental autoimmune neuritis, demyelination induced by Theiler's virus, and experimental autoimmune encephalomyelitis (EAE)—an autoimmune disease which is experimentally induced in a variety of species and which resembles multiple sclerosis in its clinical and neuropathological aspects (Gold et al., 2000; Njenga and Rodriguez, 1996).

Multiple sclerosis (MS) is the most prevalent demyelinating condition. In Europe and North America, an average of 40-100 people out of every 100,000 have MS. The disease affects approximately 250,000 people in the United States alone. MS is a chronic, devastating neurological disease that affects mostly young adults. The pathogenesis of MS is a complex process that leads to destruction of myelin and oligodendroglia, as well as axonal damage, in the brain and spinal cord (Prineas and McDonald, 1997; Trapp et al., 1998).

Histopathologically, MS is characterized by inflammation, plaques of demyelination infiltrating cells in the CNS tissue, loss of oligodendroglia, and focal axonal injury (Prineas and McDonald, 1997). The disease is thought to result from aberrant immune responses to myelin, and possibly non-myelin, self-antigens (Bar-Or et al., 1999; Hartung, 1995). Clinically, MS may follow a relapsing-remitting, or it may take a chronically progressive course with increasing physical disability (Gold et al., 2000). Typically, the symptoms of MS include lack of co-ordination, paresthesias, speech and visual disturbances, and weakness (Beers and Berkow, 1999).

Current treatments for the various demyelinating conditions are often expensive, symptomatic, and only partially effective, and may cause undesirable secondary effects. Corticosteroids (oral prednisone at 60-100 mg/day, tapered over 2-3 weeks, or intravenous methylprednisolone at 500-1000 mg/day, for 3-5 days) represent the main form of therapy for MS. While these may shorten the symptomatic period during attacks, they may not affect eventual long-term disability. Long-term corticosteroid treatment is rarely justified, and can cause numerous medical complications, including osteoporosis, ulcers, and diabetes (Id.).

Immunomodulatory therapy with recombinant human interferon-β (Betaseron and Avonex) and with co-polymer (Copaxon) slightly reduces the frequency of relapses in MS, and may help delay eventual disability (Id.). Both forms of interferon-β and co-polymer are currently used as treatment modalities for MS, but all are exceedingly expensive. Immunosuppressive drugs (azathioprine, cladribine, cyclophosphamide, and methotrexate) are used for more severe progressive forms. However, they are not uniformly beneficial, and have significant toxic side-effects. Several drugs (e.g., baclofen at 30-60 mg/day in divided doses) may reduce spasticity by inhibiting the spinal cord reflexes. Cautious and judicious use is required, though, because the drug-induced reduction in spasticity in MS patients often exacerbates weakness, thereby further incapacitating the patient (Id.).

Similarly, current treatment for adrenoleukodystrophy, another devastating demyelinating disease, is relatively ineffective. Symptoms of adrenoleukodystrophy may include cortical blindness, corticospinal tract dysfunction, mental deterioration, and spasticity. Therapy to control the course of adrenoleukodystrophy may include bone marrow transplantation and dietary treatment (DiBiase et al., 1999), but inexorable neurological deterioration invariably occurs, ultimately leading to death (Krivit et al., 1999). Some progress has been realized in the treatment of animals with EAE and experimental autoimmune neuritis, by using glial cell transplants and growth factors, and by inhibiting adhesion molecules, autoantibodies, and cytokines (Njenga and Rodriguez, 1996). However, none of these treatments has been shown to be beneficial in humans, and some require extensive neurosurgical intervention. Thus, it is clear from the foregoing that there exists a need for more effective, and less expensive and invasive, methods to treat the varied array of demyelinating conditions, without producing undesirable secondary effects.

Calcium-channel blockers are a class of pharmacological agents which inhibit the transmembrane flux of calcium ($Ca^{2+}$) ions into cells, particularly vascular smooth muscle cells and cardiac muscle cells. They have been indicated for the treatment of angina, arrhythmias, atrial fibrillation, hypertension, and paroxysmal supraventricular tachycardia (Physicians' Desk Reference, 2000). Amlodipine, a potent $Ca^{2+}$-channel blocker, is a long-acting dihydropyridine calcium antagonist (calcium ion antagonist or slow-channel blocker). Amlodipine selectively inhibits $Ca^{2+}$-ion influx across cell membranes, with a greater effect on vascular smooth muscle cells than on cardiac muscle cells. In particular, amlodipine is a peripheral arterial vasodilator that acts directly on vascular smooth muscle to cause a reduction in peripheral vascular resistance and a reduction in blood pressure. Amlodipine has been demonstrated to be effective in treating chronic stable angina, vasospastic angina, and hypertension (Id.), and it may also have neuroprotective activity (Mason et al., 1999). Other $Ca^{2+}$-channel blockers include bepridil, nitrendipine, diltiazem, felodipine, flunarizine, isradipine, mibefradil, nicardipine, nifedipine, nimodipine, nisoldipine, nivaldipine, and verapamil (Physicians' Desk Reference, 2000).

There has been a previous suggestion that calcium-channel blockers could be effective for demyelinating conditions. PCT patent publication WO 92/07564, to the Wellcome foundation ("Wellcome"), claims such a use, particularly using nimodipine. However, the skilled artisan would not consider Wellcome to be an enabling disclosure because the cell culture experiment disclosed therein would not be understood to establish the effectiveness of calcium-channel blockers for demyelinating conditions, especially inflammatory demyelinating conditions such as MS.

SUMMARY OF THE INVENTION

The present invention is predicated on the discovery that calcium-channel blockers ameliorate the clinical impairment of a demyelinating condition, experimental autoimmune encephalomyelitis (EAE), which is commonly used as a model of multiple sclerosis (MS). On the basis of these findings, the present invention provides methods for treating a demyelinating condition in a subject in need of treatment. The methods comprise administering to the subject an amount of a calcium-channel blocker effective to treat the demyelinating condition.

The invention is also directed to additional methods for treating a demyelinating condition in a subject in need of treatment. The methods comprise administering to the subject a glutamate inhibitor, in amounts effective to treat the demyelinating condition.

In related embodiments, the present invention is directed to other methods for treating a demyelinating condition in a subject in need of treatment. These methods comprise administering to the subject a calcium-channel blocker in combination with a glutamate inhibitor, in amounts effective to treat the demyelinating condition.

The invention is additionally directed to further methods for treating a demyelinating condition in a subject in need of treatment. These methods comprise administering to the subject a calcium-channel blocker in combination with a hypertensive agent, in amounts effective to treat the demyelinating condition.

In further related embodiments, the invention is directed to additional methods for treating a demyelinating condition in a subject in need of treatment. These methods comprise administering to the subject a combination of a calcium-channel blocker, a glutamate inhibitor and a hypertensive agent.

In additional embodiments, the invention is directed to pharmaceutical compositions comprising a calcium-channel blocker, a glutamate inhibitor, and a pharmaceutically-acceptable carrier.

Additionally, the invention is directed to pharmaceutical compositions comprising a calcium-channel blocker, a hypertensive agent, and a pharmaceutically-acceptable carrier.

The invention is also directed to a pharmaceutical composition comprising a calcium-channel blocker, a glutamate inhibitor, a hypertensive agent, and a pharmaceutically-acceptable carrier.

Additional objects of the present invention will be apparent in view of the description which follows.

BRIEF DESCRIPTION OF THE FIGURES

FIG. 1 illustrates the clinical course of adoptive-transfer EAE and the effect of treatment with amlodipine. SJL mice were injected with $3 \times 10^7$ MBP-activated cells. Starting from Day 5 post-immunization, mice were treated with amlodipine (30 µg as one daily subcutaneous injection) or vehicle (PBS), until Day 13 (Day 9 of treatment). Data represent mean±s.e.m. differences, at respective time-points, between the vehicle-treated group and the amlodipine-treated group. *=p<0.05; **=p<0.01 (students' unpaired, two-tailed t-test); n=8 per group.

DETAILED DESCRIPTION OF THE INVENTION

The present invention is based on the discovery, outlined in the Examples, that calcium-channel blockers are effective in reducing the effects of demyelinating conditions, in particular multiple sclerosis (MS). This discovery, and other discoveries disclosed in the Examples, demonstrate that various methods and compositions are useful for treating demyelinating conditions.

Thus, in some embodiments, the invention is directed to methods for treating a demyelinating condition in a subject in need of treatment. The methods comprise administering to the subject an amount of a formulation of a calcium-channel blocker ($Ca^{2+}$-channel blocker) effective to treat the demyelinating condition in the subject. As used herein, the term "demyelinating condition" refers to a disease, disorder, or condition characterized by loss of myelin. Examples include, without limitation, acute disseminated encephalomyelitis, acute transverse myelitis, acute viral encephalitis, adrenoleukodystrophy, adrenomyeloneuropathy, AIDS-vacuolar myelopathy, experimental autoimmune encephalomyelitis (EAE), experimental autoimmune neuritis, HTLV-associated myelopathy, Leber's hereditary optic atrophy, multiple sclerosis (MS), progressive multifocal leukoencephalopathy, subacute sclerosing panencephalitis, and tropical spastic paraparesis. Preferably, the demyelinating condition is MS.

Additionally, as used herein, the term "calcium-channel blocker" or "$Ca^{2+}$-channel blocker" refers to any one of a class of pharmacological agents, also known as calcium antagonists, which inhibit the transmembrane flux of calcium ($Ca^{2+}$) ions. As used herein, the term "agent" includes a protein, polypeptide, peptide, nucleic acid (including DNA or RNA), antibody, molecule, compound, antibiotic, drug and any combinations thereof. Numerous calcium-channel blockers are known in the art. Preferred examples of calcium-channel blockers are small molecular weight (i.e., less than about 1000 molecular weight) aromatic compounds that are known as calcium channel blockers, for example amlodipine, bepridil, nitrendipine, diltiazem, felodipine, flunarizine, isradipine, mibefradil, nicardipine, nifedipine, nimodipine, nisoldipine, nivaldipine, and verapamil. As used herein, these compounds include any non-covalent chemical derivatives of the active chemical, such as a salt, free base, hydrate, hydrochloride, etc.

As used herein, "formulation" is a preparation of an agent or combination of agents. The combination of agents can be prepared separately or mixed together.

Since the therapeutic effectiveness of these methods is based on the ability of the agent to inhibit the transmembrane flux of calcium ions, any calcium-channel blocker would be expected to provide benefit. For example, the Examples establish that three calcium-channel blockers, amlodipine, bepridil and nitrendipine, are effective. Two of those agents, amlodipine and nitrendipine, are dihydropyridine-type calcium-channel blockers, but bepridil is not chemically related to dihydropyridine or any other type of calcium-channel blocker. Although any calcium-channel blocker would be expected to be effective against demyelinating conditions, the effectiveness of any particular calcium-channel blocker could be easily tested, for example by using the methods provided in the Examples.

In these embodiments, the subject may be any mammal but is preferably a human. Preferably, the calcium-channel blocker is amlodipine, bepridil or nitrendipine.

As used herein, "amlodipine" is 3-ethyl-5-methyl-2-(2-aminoethoxymethyl)-4-(2-chlorophenyl)-1,4-dihydro-6-methyl-3,5-pyridinedicarboxylate. Synthetic amlodipine is commercially available, and can be obtained from Pfizer Inc. (New York, N.Y.). Norvasc® is the besylate salt of amlodipine. Norvasc® tablets are formulated as white tablets, equivalent to 2.5, 5, and 10 mg of amlodipine, for oral administration. Amlodipine is an affordable compound; moreover, it provides a novel approach to treating demyelinating conditions based on pathophysiologic mechanisms (Pitt et al., 2000). As with other calcium-channel blockers, though, amlodipine should be used with caution when treating subjects with heart failure (Physicians' Desk Reference, 2000).

Nitrendipine is known in the art as ethyl methyl-1,4-dihydro-2,6-dimethyl-4-(m-nitrophenyl)-3,5-pyridinedicarboxylate. It is currently not known by any brand name.

Bepridil is known in the art as [(2-methoxypropoxy)methyl]-N-phenyl-N-(phenylmethyl)-1-pyrrolidineethanamine. Bepridil is sold commercially as Vascor® (Ortho-McNeil Pharmaceutical, Inc., Raritan, N.J.), which is the monohydrochloride monohydrate form of the chemical.

In these methods, the calcium-channel blocker is administered to a subject having a demyelinating condition in an amount which is effective to treat the demyelinating condition in the subject. As used herein, the phrase "effective to treat the demyelinating condition" means effective to ameliorate or minimize the clinical impairment or symptoms of the demyelinating condition. For example, where the demyelinating condition is MS, the amount of calcium-channel blocker effective to treat the demyelinating condition is that which can ameliorate or minimize the symptoms of MS, including lack of co-ordination, paresthesias, speech and visual disturbances, and weakness. The amount of calcium-channel blocker effective to treat a demyelinating condition in a subject will vary depending on the calcium-channel blocker which is used. For example, the amount of amlodipine may range from about 5 mg/day to about 35 mg/day. Appropriate amounts of other calcium-channel blockers effective to treat a demyelinating condition in a subject can be readily determined by the skilled artisan without undue experimentation.

According to the method of the present invention, the calcium-channel blocker may be administered to a human or animal subject by known procedures, including, but not limited to, oral administration, parenteral administration, transdermal administration, and administration through an osmotic mini-pump. Preferably, the calcium-channel blocker is administered orally.

For oral administration, the formulation of the calcium-channel blocker may be presented as capsules, tablets, powders, granules, or as a suspension. The formulation may have conventional additives, such as lactose, mannitol, corn starch, or potato starch. The formulation also may be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulation also may be presented with dibasic calcium phosphate anhydrous or sodium starch glycolate. Finally, the formulation may be presented with lubricants, such as talc or magnesium stearate.

For parenteral administration, the calcium-channel blocker may be combined with a sterile aqueous solution which is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulations may be present in unit or multi-dose containers, such as sealed ampoules or vials. The formulation may be delivered by any mode of injection, including, without limitation, epifascial, intracapsular, intracutaneous, intramuscular, intraorbital, intraspinal, intrasternal, intravascular, intravenous, parenchymatous, or subcutaneous.

For transdermal administration, the calcium-channel blocker may be combined with skin penetration enhancers, such as propylene glycol, polyethylene glycol, isopropanol, ethanol, oleic acid, N-methylpyrrolidone, and the like, which increase the permeability of the skin to the calcium-channel blocker, and permit the calcium-channel blocker to penetrate through the skin and into the bloodstream. The calcium-channel blocker/enhancer compositions also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent such as methylene chloride, evaporated to the desired viscosity, and then applied to backing material to provide a patch.

The calcium-channel blocker of the present invention also may be released or delivered from an osmotic mini-pump. The release rate from an elementary osmotic mini-pump may be modulated with a microporous, fast-response gel disposed in the release orifice. An osmotic mini-pump would be useful for controlling release of, or targeting delivery of, a calcium-channel blocker, particularly a short-acting calcium-channel blocker.

The inventors have also discovered that blocking glutamate excitotoxicity mediated by AMPA/Kainate receptors are effective in reducing the effects of demyelinating conditions, in particular multiple sclerosis (MS). See Pitt et al., 2000. Accordingly, some embodiments of the present invention are directed to methods for treating a demyelinating condition in a subject in need of treatment. The methods comprise administering to the subject a formulation of a glutamate inhibitor, in amounts effective to treat the demyelinating condition. As with the calcium-channel blocker embodiments, the subject is preferably a human and the demyelinating condition is preferably MS.

As used herein, the term "glutamate inhibitor" refers to any of a class of pharmacological agents which prevent the binding and/or action of glutamate (or glutamatergic agonists) at ionotropic glutamate receptors, resulting in reduced or completely blocked ion-conductance of such receptors. Examples of appropriate glutamate inhibitors include, without limitation, carbidopa, levodopa, sodium-channel blockers, and NBQX (1,2,3,4-tetrahydro-6-nitro-2,3-dioxo-benzoquinoxaline-7-sulfonamide). The methods of administration of the calcium-channel blockers discussed above would generally be expected to be useful for administration of glutamate inhibitors.

The present invention is also directed to a method for treating a demyelinating condition in a subject in need of treatment, comprising administering to the subject a formulation of a calcium-channel blocker in combination with a glutamate inhibitor, in amounts effective to treat the demyelinating condition. The demyelinating condition may be any of those described above. The calcium-channel blocker may also be any of those described above.

In the method of the present invention, administration of a calcium-channel blocker "in combination with" another compound, in this case a glutamate inhibitor, refers to co-administration of the two compounds. Co-administration may occur concurrently, sequentially, or alternately. Concurrent co-administration refers to administration of both a calcium-channel blocker and a glutamate inhibitor at essentially the same time. For concurrent co-administration, the courses of treatment with a calcium-channel blocker and with a glutamate inhibitor may be run simultaneously. For example, a single, combined formulation, containing both an amount of a calcium-channel blocker and an amount of a glutamate inhibitor in physical association with one another, may be administered to the subject. The single, combined formulation may consist of an oral formulation, containing amounts of both a calcium-channel blocker and a glutamate inhibitor, which may be orally administered to the subject, or a liquid mixture, containing amounts of both a calcium-channel blocker and a glutamate inhibitor, which may be injected into the subject.

It is also within the confines of the present invention that a calcium-channel blocker and a glutamate inhibitor may be administered concurrently to a subject, in separate, individual formulations. Accordingly, the method of the present invention is not limited to concurrent co-administration of a calcium-channel blocker and a glutamate inhibitor in physical association with one another.

In the method of the present invention, a calcium-channel blocker and a glutamate inhibitor also may be co-administered to a subject in a formulation comprising separate, individual preparations that are spaced out over a period of time, so as to obtain the maximum efficacy of the combination. Administration of each agent may range in duration, from a brief, rapid administration to a continuous perfusion. When spaced out over a period of time, co-administration of a calcium-channel blocker and a glutamate inhibitor may be sequential or alternate. For sequential co-administration, one of the agents is separately administered, followed by the other. For example, a full course of treatment with a calcium-channel blocker may be completed, and then may be followed by a full course of treatment with a glutamate inhibitor. Alternatively, for sequential co-administration, a full course of treatment with a glutamate inhibitor may be completed, then followed by a full course of treatment with a calcium-channel blocker. For alternate co-administration, partial courses of treatment with a calcium-channel blocker may be alternated with partial courses of treatment with a glutamate inhibitor, until a full treatment of each agent has been administered.

The agents of the present invention (i.e., a calcium-channel blocker and a glutamate inhibitor, either in separate, individual formulations, or in a single, combined formulation) may be administered to a human or animal subject by any known procedures, including all of the above-described methods. Preferably, however, the calcium-channel blocker and the glutamate inhibitor are co-administered orally.

In the method of the present invention, a calcium-channel blocker and a glutamate inhibitor are co-administered in amounts effective to treat the demyelinating condition in the subject. As described above, this means that an amount of calcium-channel blocker in combination with an amount of glutamate inhibitor is effective to ameliorate or minimize the clinical impairment or symptoms of the demyelinating condition. Appropriate amounts of a calcium-channel blocker and a glutamate inhibitor effective to treat a demyelinating condition in a subject can be readily determined by the skilled artisan. A calcium-channel blocker and a glutamate inhibitor may be co-administered to a subject in order to achieve a synergistic effect in the treatment of a demyelinating condition.

Since it is well known that calcium-channel blockers reduce blood pressure, the skilled artisan would understand that it may be necessary to administer a hypertensive agent along with the calcium-channel blocker, in order to reduce the possible deleterious hypotensive effect of the calcium-channel blocker. Thus, in some embodiments, the present invention provides additional methods for treating a demyelinating condition in a subject in need of treatment. These methods comprise administering to the subject a calcium-channel blocker in combination with a hypertensive agent, in amounts effective to treat the demyelinating condition and to counter the hypotensive effect of the calcium-channel blocker. The demyelinating condition may be any of those described above. The calcium-channel blocker may also be any of those described above. Additionally, as used herein, the term "hypertensive agent" refers to any of a class of pharmacological agents which increase blood pressure. As described above, an "agent" includes a protein, polypeptide, peptide, nucleic acid (including DNA or RNA), antibody, molecule, compound, antibiotic, drug, and any combinations thereof. However, in preferred embodiments the hypertensive agent is any small molecule (i.e., less than 1000 MW) known to have a hypertensive effect. Examples of appropriate hypertensive agents include, without limitation, phenylephrine (i.e., hydroxy-$\alpha$-[(methylamino)methyl]benzyl alcohol) (particularly phenylephrine that has been carefully titrated) and sodium chloride (NaCl).

In the method of the present invention, administration of a calcium-channel blocker "in combination with" a hypertensive agent refers to co-administration of a formulation of the two agents. As described above, co-administration may occur concurrently, sequentially, or alternately. A calcium-channel blocker and a hypertensive agent may be co-administered by any of the above-described methods, and in any of the above-described formulations. For example, for concurrent co-administration, as described above, the courses of treatment with a calcium-channel blocker and with a hypertensive agent may be run simultaneously, in a single, combined formulation containing both an amount of a calcium-channel blocker and an amount of a hypertensive agent in physical association with one another. Alternatively, as described above, an amount of a calcium-channel blocker and an amount of a hypertensive agent may be administered concurrently to a subject, in separate, individual preparations. Accordingly, the method of the present invention is not limited to concurrent co-administration of a calcium-channel blocker and a hypertensive agent in physical association with one another.

In the method of the present invention, a calcium-channel blocker and a hypertensive agent also may be co-administered to a subject in separate, individual preparations that are spaced out over a period of time, so as to obtain the maximum efficacy of the combination. Administration of each agent may range in duration, from a brief, rapid administration to a continuous perfusion. When spaced out over a period of time, co-administration of a calcium-channel blocker and a hypertensive agent may be sequential or alternate, as described above.

The agents of the present invention (i.e., a calcium-channel blocker and a hypertensive agent, either in separate, individual preparations, or in a single, combined formulation) may be administered to a human or animal subject by any known procedures, including all of the above-described methods. Preferably, however, the calcium-channel blocker and the hypertensive agent are co-administered orally.

In the method of the present invention, a calcium-channel blocker and a hypertensive agent are co-administered in amounts effective to treat the demyelinating condition in the subject. As described above, this means that an amount of calcium-channel blocker in combination with an amount of hypertensive agent is effective to ameliorate or minimize the clinical impairment or symptoms of the demyelinating condition. Appropriate amounts of a calcium-channel blocker and a hypertensive agent effective to treat a demyelinating condition in a subject can be readily determined by the skilled artisan. A calcium-channel blocker and a hypertensive agent may be co-administered to a subject in order to achieve a synergistic effect in the treatment of a demyelinating condition.

Based on the discussion above pertaining to combinations of calcium-channel blockers with glutamate inhibitors or hypertensive agents, it would also be understood that combinations of these three agents can be used to treat demyelinating conditions. Thus, the invention is directed to additional methods for treating a demyelinating condition in a subject in need of treatment. These methods comprise administering to the subject an amount of an agent effective to treat the demyelinating condition, where the agent is a combination of calcium-channel blocker, a glutamate inhibitor and a hypertensive agent.

It is within the confines of the present invention that the formulations of a calcium-channel blocker and a glutamate inhibitor, a calcium-channel blocker and a hypertensive agent, or a calcium-channel blocker, glutamate inhibitor and a hypertensive agent (whether individual or combined for any of these formulations) may be further associated with a pharmaceutically-acceptable carrier, thereby comprising a pharmaceutical composition. Accordingly, the present invention is also directed to pharmaceutical compositions comprising a calcium-channel blocker, a glutamate inhibitor, and a pharmaceutically-acceptable carrier; in other embodiments the pharmaceutical composition is a calcium-channel blocker, a hypertensive agent, and a pharmaceutically-acceptable carrier; in still other embodiments the pharmaceutical composition is a calcium-channel blocker, a glutamate inhibitor, a hypertensive agent and a pharmaceutically-acceptable carrier. Any of these pharmaceutical compositions would be useful for treating a demyelinating condition in a subject in need of treatment. Where the pharmaceutical composition is administered to a subject to treat a demyelinating condition, the calcium-channel blocker and a glutamate inhibitor are provided in amounts which are effective to treat the demyelinating condition.

The pharmaceutically-acceptable carrier of the present invention must be "acceptable" in the sense of being compatible with the other ingredients of the composition, and not deleterious to the recipient thereof. Examples of acceptable pharmaceutical carriers include carboxymethylcellulose, crystalline cellulose, glycerin, gum arabic, lactose, magnesium stearate, methyl cellulose, powders, saline, sodium alginate, sucrose, starch, talc, and water, among others. Formulations of the pharmaceutical composition may conveniently be presented in unit dosage.

The formulations of the present invention may be prepared by methods well-known in the pharmaceutical art. For example, the active compound may be brought into association with a carrier or diluent, as a suspension or solution. Optionally, one or more accessory ingredients (e.g., buffers, flavoring agents, surface active agents, and the like) also may be added. The choice of carrier will depend upon the route of administration. The pharmaceutical composition would be useful for administering the calcium-channel blocker and the glutamate inhibitor of the present invention (either in separate, individual formulations, or in a single, combined formulation) to a subject to treat a demyelinating condition. The agents are provided in amounts that are effective to treat a demyelinating condition in the subject. These amounts may be readily determined by the skilled artisan.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

Treatment of Experimental Autoimmune Encephalomyelitis with Amlodipine

Materials and Methods

Induction of Experimental Autoimmune Encephalomyelitis (EAE). Adoptive-transfer EAE was induced in female SJL mice as described (Cannella et al., 1998). In brief, lymph node cells were obtained 10 days after myelin basic protein/Complete Freund's Adjuvant immunization. Cells were cultured for 4 days with 50 µg/ml of myelin basic protein, then $3 \times 10^7$ cells/mouse were injected into syngeneic mice via tail veins. Onset of disease occurred after 7-9 days. Animals were graded according to a standard clinical index (0-5). Five days after immunization, animals began treatments with one daily injection of 200 µl of vehicle (PBS), or 30 µg of amlodipine in 200 µl of PBS.

Neuropathology. At selected time-points, mice from the control and treated groups were perfused with PBS or glutaraldehyde, and the CNS was prepared for frozen or 1-µm epoxy sections, respectively. Epoxy sections were stained with toluidine blue, and examined by light microscopy. Frozen sections were used for immunohistochemistry to evaluate damage to oligodendrocytes and neurons.

Results and Discussion

Multiple sclerosis (MS) is characterized by destruction of myelin and oligodendrocytes in the CNS, as discussed above. One of the primary tools in MS research is experimental autoimmune encephalomyelitis (EAE), a demyelinating condition in animals which mimics many important aspects of the clinical and pathological features of MS (Prineas and McDonald, 1997; Gold et al., 2000). The mechanisms in MS which lead to myelin destruction and the demise of oligodendrocytes are currently unknown. Possible candidates are cell-cell contact involving inflammatory cells, and soluble factors such as TNF-α (Akassoglou et al., 1998), metalloproteinases (Liedtle et al., 1998), reactive oxygen species (e.g., $O_2^-$ and $ONOO^-$) (Kolb and Kolb-Bachofen, 1992), and autoantibodies (Genain et al., 1999). One soluble compound in particular, which is released in large quantities by activated leukocytes and microglia, has received little attention: glutamate. In activated immune cells, glutamate is produced and released by enzymatic breakdown of glutamine (Piani et al., 1991; Pithon et al., 1997). However, in animals with EAE, glutamate degradation by astroglial glutamine synthase and glutamate dehydrogenase is diminished (Hardin-Pouzet et al., 1997). These findings suggest an increased extracellular glutamate concentration in and around the infiltrative lesion. This increase in glutamate is potentially disastrous in the mammalian CNS. The extracellular concentration of glutamate is tightly controlled in the CNS, and the glutamate gradient between extracellular and intracellular space is about 1:1000. If present in larger quantities, extracellular glutamate can cause excitotoxic cell death by overstimulation of the cellular ionotropic glutamate receptors, the NMDA and the AMPA/Kainate receptors (Rothman and Olney, 1987; McDonald et al., 1998).

The inventors have also discovered that glutamate excitotoxicity mediated by AMPA/Kainate receptors accounts for a substantial portion of CNS damage in EAE (Pitt et al., 2000). Blockage of AMPA/Kainate receptors by NBQX, a prototypical AMPA/Kainate receptor antagonist, significantly ameliorated the course of the disease and reduced loss of oligodendrocytes and axonal damage. However, it was demonstrated, both in vitro and in vivo, that NBQX did not overtly affect the activity of the immune system (Pitt et al., 2000). Thus, the observed improvement resulted from direct protection against AMPA/Kainate-receptor-mediated excitotoxicity, rather than suppression of the immune response.

An important event downstream of AMPA/Kainate-receptor-mediated excitotoxicity is the opening of voltage-sensitive $Ca^{2+}$ channels, with subsequent excess $Ca^{2+}$ influx, which results in $Ca^{2+}$ overload and eventual excitotoxic damage (Choi, 1988). Since the inventors had previously established a role for AMPA/Kainate receptor-mediated excitotoxicity in EAE, they investigated whether blockage of voltage-sensitive $Ca^{2+}$ channels might similarly reduce excitotoxic damage in this animal model of MS. The calcium-channel antagonist amlodipine was selected for this study because of its long half-life in vivo (>30 h), and the beneficial effect on excitotoxic damage which it was shown to have in an in vitro model for excitotoxicity (Mason et al., 1999).

Figure 1:
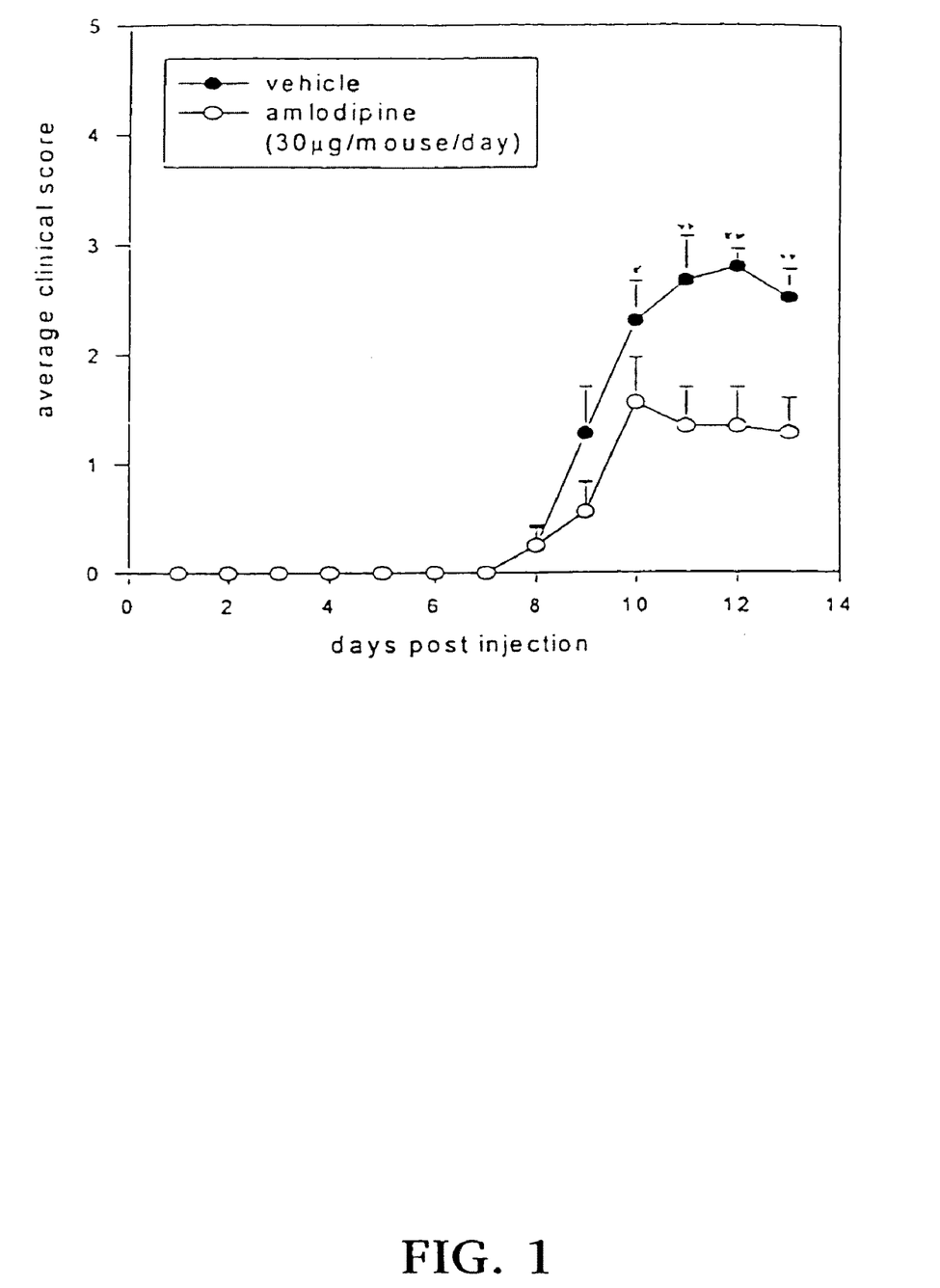

As the results of the present investigation show, 30 µg/day of amlodipine (in 200 µl of phosphate buffered saline [PBS]) significantly ($p<0.01$) ameliorated clinical impairment in the acute phase of the adoptive-transfer model of EAE. Mice (n=8) were treated from Day 5 post-immunization. The control group (n=8) received one daily subcutaneous injection of 200 µl of the vehicle PBS. The difference in clinical score was significant at Day 4 after onset of the disease, and continued to increase until the time of sampling (FIG. 1). The CNSs of two representative animals of each group were taken and examined as 1-µm epoxy sections stained with toluidine blue. The animals differed considerably in their clinical scoring, with an average score of 1.3 (amlodipine group) and 2.8 (control group). However, the examination of sections from the entire neuraxis (10 levels) showed a similar degree of inflammation and demyelination in both groups. This indicated that amlodipine does not modulate the inflammatory process itself—a result similar to that which was found with NBQX treatment.

In conclusion, the results show that amlodipine significantly ($p<0.01$) ameliorated the clinical impairment in acute EAE. However, examination of the neuraxis in both vehicle- and amlodipine-treated animals showed similar degrees of inflammation, indicating that amlodipine does not affect inflammation. The reduction in clinical impairment is, therefore, most likely due to amlodipine's protecting CNS cells against glutamate excitotoxicity via blockage of voltage-sensitive $Ca^{2+}$ channels.

EXAMPLE 2

Additional Calcium Channel Blockers Ameliorate Disease in a Mouse Model of Multiple Sclerosis An abstract describing portions of this work was published in J. Neurochem. 81:50 (2002), and presented at the Meetings of the American Society of Neurochemistry, Jun. 22-27, 2002.

Example Summary

Multiple sclerosis (MS) and experimental autoimmune encephalomyelitis (EAE), an animal model of MS, are inflammatory demyelinating diseases of the central nervous system. The inflammatory attacks lead to glial dysfunction and death, axonal damage and neurological deficits. Numerous in vitro studies suggest that extracellular calcium influx, via voltage-gated calcium channels, contributes to white matter damage in acute spinal cord injury and stroke. We hypothesized that this mechanism is also operative in EAE, and, possibly, MS. In our study, administration of the calcium-channel blockers bepridil and nitrendipine significantly ameliorated EAE in mice, compared with vehicle treated controls. Spinal cord samples showed reduced axonal destruction in bepridil-treated animals in spite of monocyte infiltration to the CNS. Direct protection of axons by calcium-channel blockers is supported by our immunohistochemical finding that mouse spinal cord axons express subunits of L-type voltage-gated calcium-channel. Our data support the hypothesis that calcium influx via voltage gated calcium channels plays a significant role in the development of neurological disability and white matter damage in EAE and MS.

Introduction

Multiple sclerosis (MS) is an immune-cell mediated inflammatory demyelinating disease of the central nervous system (CNS). MS and experimental autoimmune encephalomyelitis (EAE), an animal model of MS (Juhler, 1988), are characterized by disturbed central nerve conductance leading to motor and sensory impairments. Pathological findings in MS (Ewing and Bernard, 1998) and EAE (Juhler, 1988) include infiltration of activated peripheral inflammatory cells into the CNS (Raine et al., 1984), loss of myelin (Lassman, 1999), edema (Levine et al., 1966) and axonal damage (Kornek et al., 2000).

Revealing the still elusive mechanisms that lead to pathological changes in MS would facilitate the therapeutic amelioration of white matter damage, thus improving neural function. Studies on models of white matter injury have suggested that depolarization and ion balance disturbances, culminating in increased intracellular calcium concentration, lead to disrupted axonal function (Rosenberg et al., 1999; Stys and Lopachin, 1998). Decreasing extracellular calcium concentration also protects rat optic nerve from anoxia (Waxman et al., 1993). Protection of spinal cord dorsal columns from anoxia (Li et al., 2000) or optic nerve against ischemic injury (Stys and Lopachin, 1998) was evident when inhibitors of $Na^+/Ca^{2+}$ exchange were used. Similarly, spinal cord white matter damage was attenuated by a variety of voltage gated calcium channel blockers in models of anoxia (Brown et al., 2001; Imaizumi et al., 1999) and traumatic injury (Agrawal et al., 2000).

The above findings, together with the fact that calcium channels are present on cellular elements (Id.; Brown et al., 2001; Liu et al., 1997) that are key targets in autoimmune demyelination, raise the following question: can calcium antagonists be useful in ameliorating inflammatory demyelination?

Several lines of evidence support the notion that aberrations in ionic balance of white matter constituents contribute to the pathophysiology in MS and EAE (Claudio et al., 1990; Wakefield et al., 1994; Wender et al., 2000). Studies in EAE and MS tissue have suggested that involvement of mechanisms such as activation of ionotropic glutamate receptors (Matute et al., 1999; Pitt et al., 2000) and sodium channels (Rosenberg et al., 1999) lead to excessive calcium influx.

Experimental

We tested the hypothesis that increased influx of extracellular calcium through voltage-gated calcium channels contributes to the neurological impairment and pathological outcome in EAE, and, by inference, MS. For this, we used two different calcium antagonists, bepridil and nitrendipine. Bepridil is a broad-range calcium-channel blocker with a strong inhibitory effect on $Na^+/Ca^{2+}$ exchange and on sodium channels (Gill et al., 1992). In contrast, the dihydropyridine-type calcium-channel blocker nitrendipine is a rather selective blocker of L-type voltage-gated calcium channels (Merck Index, 1989). We studied the effect of these drugs on disease onset and progression using passive, i.e. adoptive transfer, EAE (AT-EAE). AT-EAE, unlike directly induced (active) EAE, is induced by the transfer of fully antigen-primed, myelin basic protein-targeted T-cells to recipient animals (Raine et al., 1984). These primed T-cells are clonally expanded in vitro before the transfer, thus bypassing the initial sensitization phase of the disease and reducing the possible interference of drug treatment with development of autoimmunity (Glabinski et al., 1997).

We used female SJL/J mice (Jackson Laboratories, Bar Harbor, ME). They were housed in a light- and temperature-controlled environment in accordance with NIH and AAA-LAC guidelines. All experiments were performed under an institutionally approved animal protocol. The antigen was myelin basic protein, a component of myelin, (1 mg/mouse; Sigma, St. Louis, Mo.) dissolved in sterile PBS and emulsified with an equal volume of incomplete Freund's adjuvant supplemented with *Mycobacterium tuberculosis* (55 µg/mouse; Difco, Detroit, Mich.). The emulsion (200 µL/mouse) was injected into the flanks of 11 weeks old mice. Lymph node cells were obtained from draining lymph nodes 10 days later. Lymph node cells were cultured for 4 days in RPMI-1640 (Gibco-BRL) medium in the presence of myelin basic protein (75 µg/ml). Cultured lymph node cells were subsequently injected into the tail vein of syngeneic 6 weeks old SJL/J mice at a dose of $4 \times 10^7$ cells/mouse. Onset of disease in control animals occurred after 8-10 days. In this animal model of MS, the immune attack manifests in a predictable pattern of ascending paralysis that correlates with the degree of spinal cord inflammation and edema (Simmons et al., 1982). Disability was scored daily as follows: 0—no clinical signs, 1—flaccid tail, 2—abnormal gait, 3—hind limb paralysis, 4—complete paralysis, 5—moribund or dead. Spinal cord tissue, harvested at the peak of disability, was processed for pathological assessment using 1 µm epoxy sections. Animals, with scores representative of each group, were perfused with glutaraldehyde and processed as described (Mokhtarian et al., 1984). Epoxy-embedded 1 µm sections were stained with toluidine blue, and examined under a light microscope (Olympus IX-70, 40× objective). For immunohistochemistry, we used longitudinal freshly-frozen 10 µm sections from phosphate-buffered saline perfused naive animals, subsequently post-fixed with acetone. Sections were double-labeled using SM131 antibody (1:10,000; Sternberger Monoclonals, Md.) for axonal NF-H and a polyclonal anti-Voltage-gated calcium channels subunit α1D (1 µg/ml; Alomone Labs, Jerusalem, Israel). These primary antibodies were reacted for 1 hour with Texas Red-conjugated anti-mouse (1:500) and biotinylated anti-rabbit (1:800) antibodies, respectively. Biotinylated secondary antibody was visualized by incubating for 1 hour with streptavidin conjugated Alexafluor 488 (Molecular Probes, Eugene, Oreg.) at a dilution of 1:2000. Images were acquired using a Bio-Rad (Hercules, Calif.) Radiance 2000 confocal with Nikon (Melville, N.Y.) Eclipse 200 microscope using a 60×N.A. 1.4 planpo objective. A Kr/Ar laser excitation at 488 nm and 568 nm and narrow pass filters detected green and red probes, respectively. For statistical comparison of treatment groups we used ANOVA followed by multiple comparisons using the statistical program Prism 3.0 (Graphpad, San Diego, Calif.). A p-value of less than 0.05 was considered significant.

Figure 3:
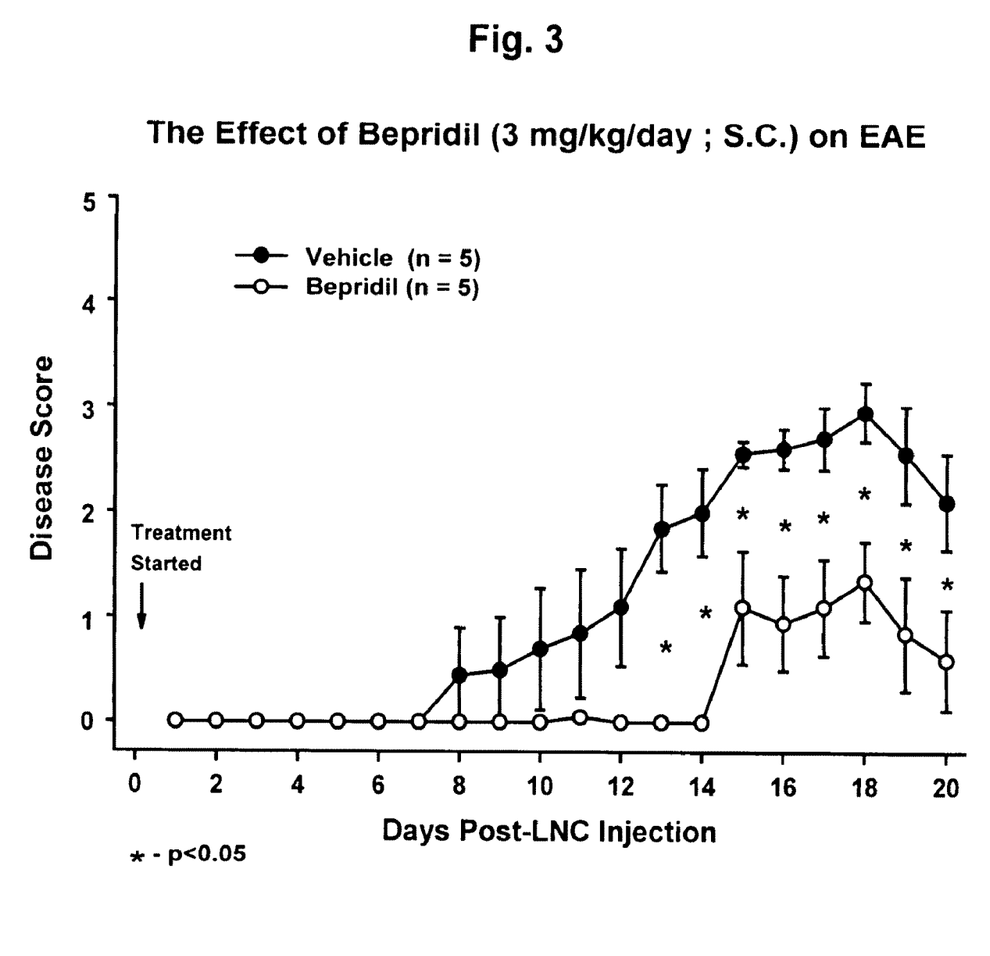
FIG. 3 is a graph summarizing experiments that establish that bepridil administration beginning on the same day of disease induction attenuates adoptive-transfer EAE. Mice receiving bepridil (3 mg/kg; open circles) starting at the day of treatment showed a significantly reduced neurological disability compared with mice treated with corresponding vehicle (closed circles). The significance of differences in disease score between treatment groups was assessed by analysis of variance followed by multiple comparisons.
Figure 4:
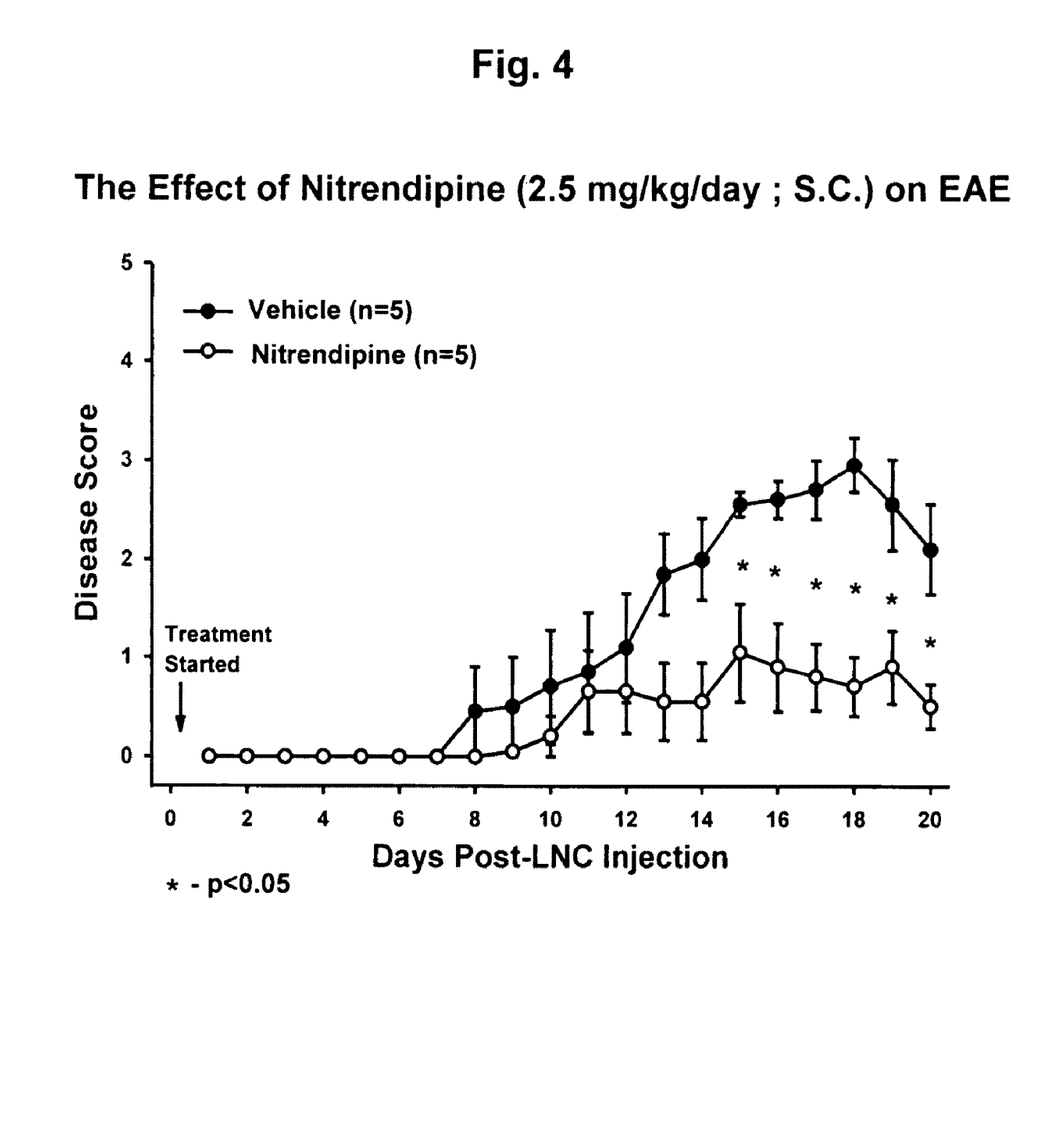
FIG. 4 is a graph summarizing experiments that establish that nitrendipine administration on the same day of disease induction attenuates adoptive-transfer EAE. Mice receiving nitrendipine (2.5 mg/kg; open circles) starting at the day of treatment showed a significantly reduced neurological disability compared with mice treated with corresponding vehicle (closed circles). The significance of differences in disease score between treatment groups was assessed by analysis of variance followed by multiple comparisons.

Bepridil (3 mg/kg; s.c.), nitrendipine (2.5 mg/kg; s.c.) and vehicle were administered daily, starting on the day of lymph node cell-transfer (day 0). Bepridil treatment, from day 0, delayed overt disease onset by more than 5 days compared with vehicle (FIG. 3), and reduced the clinical impairment beginning at day 10 post lymph node cell-transfer (p.t.). This difference was statistically significant from day 13 p.t. onward (p<0.05), continuing into both the plateau phase (days 15-18 p.t.) and the remission phase of the disease (days 19-20 p.t.). Bepridil reduced daily average disease scores by 1.8, 2.0, 1.45, 1.65, 1.60, 1.60, 1.70 and 1.5 points (average −1.66±0.06) on days 13-20 p.t., respectively. With nitrendipine treatment starting at day 0, clinical progression was also slower and reduced when compared with vehicle treated animals (FIG. 4). Average disability scores for the nitrendipine group were lower than corresponding vehicle beginning on day 13 p.t., and this difference became significant (p<0.05) from day 15 p.t. Nitrendipine ameliorated the clinical impairment by 1.5, 1.7, 1.9, 2.25, 1.65 and 1.6 points (average −1.77±0.11) on days 15-20 p.t., respectively. There was no statistically significant difference in disability scores between bepridil and nitrendipine groups.

Figure 2:
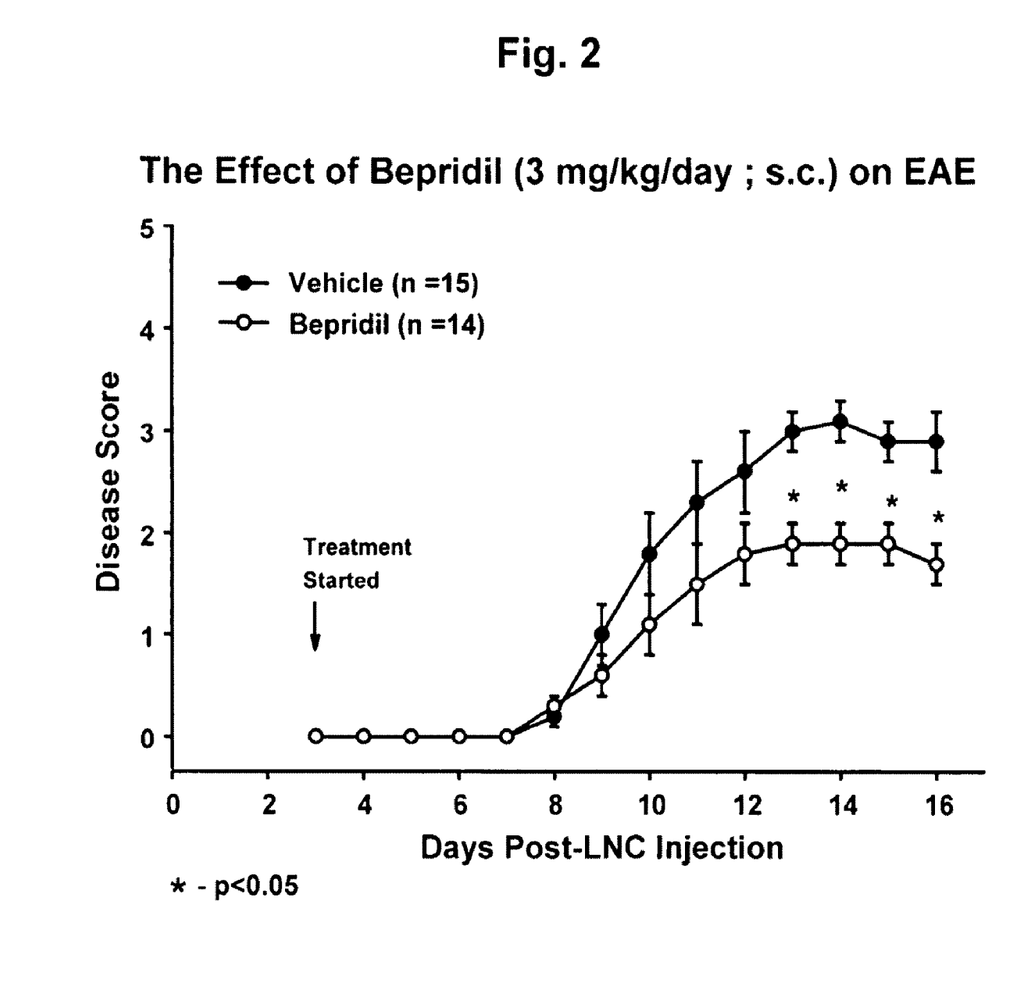
FIG. 2 is a graph summarizing experiments that establish that bepridil administration beginning at day 3 after disease induction attenuates adoptive-transfer EAE. Mice receiving bepridil (3 mg/kg; open circles) starting at day 3 post-treatment showed a significantly reduced neurological disability compared with mice treated with corresponding vehicle (closed circles). The significance of differences in disease score between treatment groups was assessed by analysis of variance followed by multiple comparisons.
Figure 5:
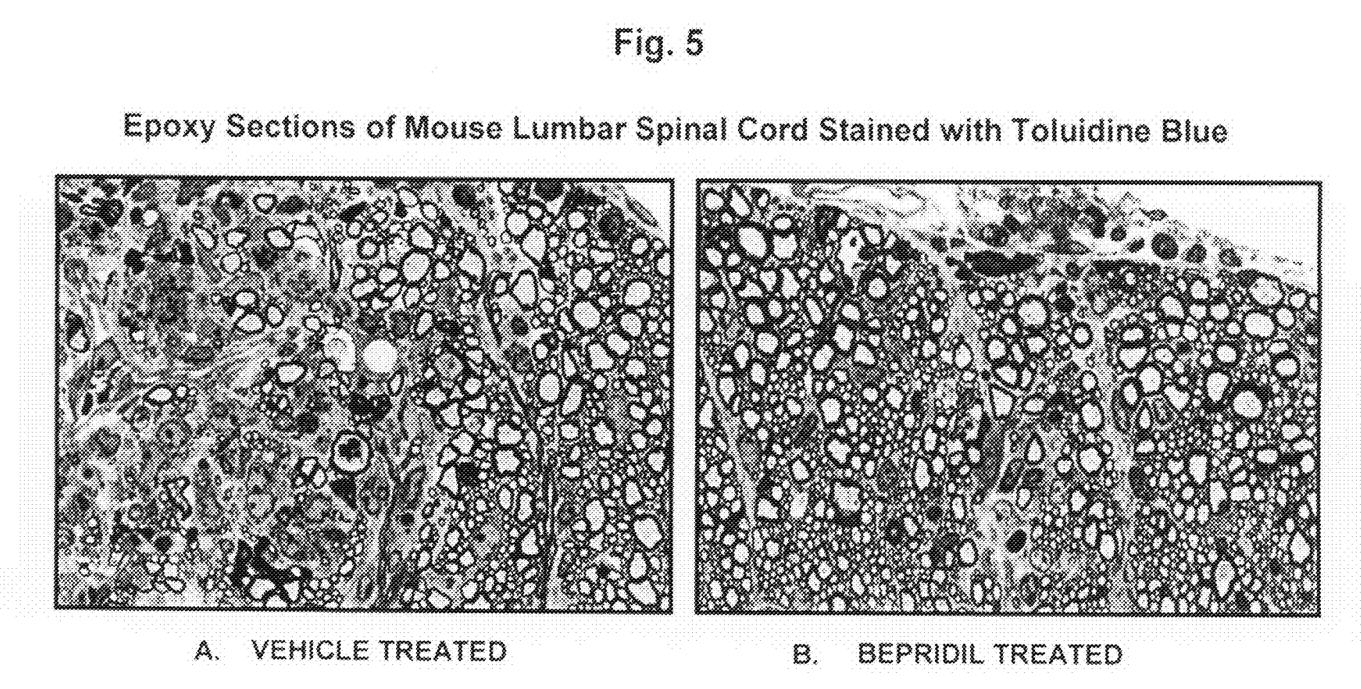
FIG. 5 shows micrographs of vehicle- (Panel A) and bepridil-(Panel B) treated mice with adoptive transfer EAE. Vehicle treated mice with adoptive transfer EAE (Panel A) have widespread regions which are infiltrated with monocytes and are devoid of axons. These regions are flanked by areas that contain axons with abnormal myelin (asterisk). On the right, a region with many intact axons. Bepridil treated mice with adoptive transfer EAE (Panel B) have fewer infiltrating cells with only sporadic axonal abnormalities (asterisk).

Studies in various EAE models have demonstrated that the timing of pharmacological intervention is a major determinant in the effectiveness of treatment (Fujimoto et al., 1999; Jung et al., 1996; Niino et al., 2001). Therefore, we tested whether the mechanisms of damage and disability will respond to treatment when it is initiated later in the course of the disease. When we started treating mice on day 5 p.t., instead of on day 0, neither bepridil nor nitrendipine altered disease onset or disability compared with vehicle control animals (data not shown). In contrast, bepridil administration, initiated on day 3 p.t. (n=14), reduced neurological impairment significantly (p<0.05) from day 13 p.t. to day 16 p.t. (the day tissue was harvested), compared with vehicle controls (n=15)(FIG. 2). The difference in average disease scores between vehicle and bepridil groups was 1.07, 1.20, 0.99 and 1.18 points (average −1.11±0.05) on days 13-16 p.t., respectively. In both treatment schedules (starting on day 0 or on day 3 p.t.), the difference between vehicle control and bepridil treatment became significant on day 13 p.t. This difference was larger when treatment started on day 0 rather than on day 3 p.t. (difference in average disease scores 1.66±0.06 vs. 1.11±0.05, respectively) (FIG. 3). These data suggest a decreasing efficacy for calcium antagonists, as the disease progresses, with the inflammatory attack reaching a 'point of no return' between day 3 and 5 p.t. These data are in accordance with Morrissey et al. (1996) who reported that, following myelin basic protein-primed T-cells administration to rats, the major increase in immune cell counts occurred between days 3 and 5 p.t. However, in our study, when bepridil was given 3 days p.t., it did not completely prevent monocyte infiltration into the CNS, and myelin and axonal damage adjacent to the infiltrating cells was evident (FIG. 5). Therefore, it seems unlikely that the ameliorative effect of calcium-channel blockers was due to interference with immune cell recruitment, although it cannot be ruled out.

Another possible mechanism for calcium-channel blocker amelioration of AT-EAE is by direct protection of white matter constituents. In our initial histological data (FIG. 5), axonal loss was more pronounced in spinal cords taken from vehicle vs. from bepridil-treated animals. Since the common mechanism for bepridil and nitrendipine is blockade of L-type voltage-gated calcium channels, we used immunohistochemistry to determine whether L-channels are expressed in SJL/J mouse spinal cord white matter. We found abundant overlap of α1D labeling with axons (data not shown). Control sections for which anti-α1D antibody was pre-adsorbed with the peptide used to raise the antibody, showed no immunoreactivity to the α1D antibody, confirming the specificity of the labeling. Our finding is in agreement with Brown et al. (2001) who detected L-channel subunits in rat optic nerve axons. Whether these axonal L-channel subunits are found in the axolemma and form functional channels is still to be determined.

In summary, two structurally and functionally different calcium antagonists, bepridil and nitrendipine, had comparable beneficial effects on AT-EAE in mice. They delayed the onset of disability and significantly reduced the maximum neurological impairment in this animal model of MS. Both drugs, although different in many other respects, block calcium influx through L-type calcium channels. Therefore, it is likely that this mechanism plays a significant role in the tissue damage and the development of neurological disability in inflammatory demyelinating conditions such as EAE and MS. Our data also supports the notion that axons may be a direct target for calcium influx via voltage-gated calcium channels in EAE and MS (Komek et al., 2001). Modulation of calcium influx, either by direct blockade of calcium channels or by preventing upstream excessive depolarization, may be of therapeutic value in MS.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method for reducing neurological disability associated with multiple sclerosis in a subject in need of such treatment, the method comprising administering to the subject an amount of a calcium-channel blocker effective to reduce the neurological disability associated with multiple sclerosis in the subject, wherein the calcium channel blocker is amlodipine, bepridil, felodipine, isradipine, nicardipine, nifedipine, nisoldipine or nivaldipine.

2. The method of claim 1, wherein the neurological disability results in lack of coordination, paresthesias, speech, visual disturbances and/or weakness.

3. A method for reducing neurological disability associated with multiple sclerosis in a subject in need of such treatment, the method comprising administering to the subject an amount of a calcium-channel blocker effective to reduce neurological disability associated with multiple sclerosis in the subject, wherein the calcium channel blocker is amlodipine, bepridil or nitrendipine.

4. The method of claim 1, wherein the calcium channel blocker is felodipine.

5. The method of claim 1, wherein the calcium channel blocker is isradipine.

6. The method of claim 1, wherein the calcium channel blocker is nicardipine.

7. The method of claim 1, wherein the calcium channel blocker is nifedipine.

8. The method of claim 1, wherein the calcium channel blocker is nisoldipine.

9. The method of claim 1, wherein the calcium channel blocker is nivaldipine.

* * * * *